(12) United States Patent
Brown

(10) Patent No.: US 7,455,847 B1
(45) Date of Patent: Nov. 25, 2008

(54) PIGMENTED COSMETIC COMPOSITION AND METHODS RELATED THERETO

(75) Inventor: Richard Allen Brown, Northridge, CA (US)

(73) Assignee: Comestic Laboratories of America, A Division of St. Ives Laboratories, Inc., Melrose Park, IL (US)

( * ) Notice: Subject to any disclaimer, the term of this patent is extended or adjusted under 35 U.S.C. 154(b) by 457 days.

(21) Appl. No.: 10/047,817

(22) Filed: Jan. 15, 2002

Related U.S. Application Data

(60) Provisional application No. 60/270,047, filed on Feb. 20, 2001.

(51) Int. Cl.
*A61K 8/02* (2006.01)
*A61K 9/00* (2006.01)
*A61K 8/00* (2006.01)
*A61K 8/18* (2006.01)
*A61Q 1/02* (2006.01)
*A61Q 19/04* (2006.01)

(52) U.S. Cl. .......................... 424/401; 424/400; 424/63

(58) Field of Classification Search ............... 424/63, 424/59, 64, 401, 400

See application file for complete search history.

(56) References Cited

U.S. PATENT DOCUMENTS

| | | | | |
|---|---|---|---|---|
| 5,143,722 A | * | 9/1992 | Hollenbery et al. | 424/63 |
| 5,162,378 A | * | 11/1992 | Guthauser | 514/785 |
| 5,599,533 A | * | 2/1997 | Stepnieski et al. | 424/78.02 |
| 5,656,672 A | * | 8/1997 | Collin et al. | 514/725 |
| 5,730,991 A | * | 3/1998 | Rapaport | 424/401 |
| 5,882,661 A | * | 3/1999 | Dorogi et al. | 424/401 |

OTHER PUBLICATIONS www.ucalgary.ca/~schramm/emulsion.htm.*

* cited by examiner

*Primary Examiner*—Sreeni Padmanabhan
*Assistant Examiner*—Uma Ramachandran
(74) *Attorney, Agent, or Firm*—Leydig, Voit & Mayer, Ltd.

(57) ABSTRACT

A pigmented cosmetic composition comprising a water-in-oil emulsion is disclosed. The composition includes a continuous oil phase, an aqueous phase, pigment, emulsifier, and a separation inhibitor comprising a silicone elastomer. The silicone elastomer optionally can be included in a carrier. Also disclosed are a method of inhibiting separation of a pigmented cosmetic composition comprising a water-in-oil emulsion, and a method of preparing a pigmented cosmetic composition.

32 Claims, No Drawings

PIGMENTED COSMETIC COMPOSITION AND METHODS RELATED THERETO

CROSS-REFERENCE TO RELATED PATENT APPLICATIONS

This patent application claims the benefit of U.S. Provisional Patent Application No. 60/270,047, filed Feb. 20, 2001, the contents of which are hereby incorporated by reference.

TECHNICAL FIELD OF THE INVENTION

The present invention relates generally to pigmented cosmetic compositions. In particular, the present invention relates to a pigmented composition comprising a water-in-oil emulsion that exhibits improved stability, as well as methods related thereto.

BACKGROUND OF THE INVENTION

Many cosmetic products are in the form of water-in-oil emulsions because they permit uniform application, and because they provide good coverage, as well as good skin feel, wear, and appearance. For example, many types of make-ups, such as, for example, foundation, mascara, eyeshadow, eye-liner, rouge, concealer, lipstick, lipcolor, and the like, often are in the form of water-in-oil emulsions. Generally, such products are used to apply color, mask imperfections, provide some visual effect, such as a glowing effect, and the like in order to enhance the beauty of the user. In addition, many types of pigmented sunscreens, or "particulate" sunscreens, are in the form of water-in-oil emulsions where the pigment is "invisible" and is included to protect the skin from potentially damaging sun rays, rather than to apply color to the skin to enhance beauty.

Despite the aesthetic and application attributes provided by such pigmented water-in-oil emulsion products, a significant problem with such products is that they tend to separate over time due to the presence of the pigment particulate, which is much heavier than the aqueous and oil phases. In this respect, although a typical water-in-oil emulsion that is absent pigment particulate generally will remain stable, the inclusion of the relatively heavy pigment particulate tends to destroy the emulsion because of the weight difference of the pigment as compared with the oil and aqueous phases. As a result, the aqueous phase, oil phase, and pigment particulate separate such that they no longer are uniformly distributed in the product's container. Generally, after packaging of the product, the water travels to the top of the container, creating a relatively clear surface layer, while the pigment travels to the bottom of the container. Although the user can attempt to compensate for the separation by shaking the container prior to application, it nevertheless is difficult for the user to achieve a uniform application, thereby diminishing the application and aesthetic qualities of the product.

Previous attempts to minimize separation in pigmented water-in-oil cosmetic products have not met with success. For example, one approach has been to include thickener, such as metal soaps and the like, to increase the viscosity of the product in an attempt to fix in place the water droplets and pigment in the continuous oil phase. However, the addition of such conventional thickeners to the water-in-oil emulsions only results in short-term benefits, and such products still tend to separate over time. In addition, separation in conventionally thickened formulations can be triggered in response to exposure to elevated temperatures, such as, for example, temperatures above about 40° C. Furthermore, enhancement of the thickness can diminish some of the product's aesthetic properties, such as its desired feel and its ability to be uniformly applied.

Another disadvantage with conventional water-in-oil emulsion cosmetic products relates to their manufacture. For example, such products typically require the use of pigment blends in order to produce a final color which may vary depending upon the desired tone of the user. However, conventional manufacturing techniques are inefficient because they do not permit the mixing of two or more water-in-oil emulsions of different colors because of the tendency of the emulsions to separate. In view of the size requirements of existing manufacturing equipment, conventional water-in-oil emulsion cosmetic products are prepared in one large batch with the pigments blended therein during processing. Thus, conventional manufacturing techniques for preparing pigmented water-in-oil emulsion products are ill-suited for making varying quantities of product, particularly lower quantities, because of the lack of versatility in manufacture caused by the difficulty in mixing more than one pigmented water-in-oil emulsion together.

Accordingly, it will be appreciated from the foregoing that there is a need in the art for a pigmented cosmetic composition comprising a water-in-oil emulsion that does not separate readily, particularly over time, while maintaining desired application, feel, coverage, wear, and appearance characteristics. There also is a need for a pigmented cosmetic composition that is able to remain stable even upon exposure to elevated temperatures. It will also be appreciated that there is a need for a method of preparing the cosmetic composition where two or more pigmented water-in-oil emulsions, for example, of differing colors, can be blended together to achieve a final product.

BRIEF SUMMARY OF THE INVENTION

The present invention provides a pigmented cosmetic composition comprising a water-in-oil emulsion, a method of inhibiting separation of a pigmented cosmetic composition comprising a water-in-oil emulsion, and a method of preparing a pigmented cosmetic composition.

It has been found that including a silicone elastomer in a pigmented cosmetic composition comprising a water-in-oil emulsion inhibits separation of the resulting product, even over long periods of time. Thus, in one aspect, the present invention provides a pigmented cosmetic composition comprising a water-in-oil emulsion, and a method of inhibiting separation in such an emulsion. The emulsion comprises a continuous oil phase, an aqueous phase, a pigment, an emulsifier, and a separation inhibitor comprising a silicone elastomer. In some embodiments, the separation inhibitor also can include a carrier for the silicone elastomer.

In another aspect of the present invention, a method of preparing a pigmented composition is provided. The method comprises preparing a first water-in-oil emulsion comprising a continuous oil phase, an aqueous phase, an emulsifier, a pigment, and a separation inhibitor comprising a silicone elastomer. In addition, the method comprises preparing a second water-in-oil emulsion comprising a second oil phase, a second aqueous phase, a second emulsifier, and a second pigment. Preferably, the second water-in-oil emulsion also includes a silicone elastomer. In some embodiments, each of the aqueous phase, oil phase, emulsifier, and silicone elastomer of the two emulsions are the same, while the pigments are different. The method also comprises mixing the first water-in-oil emulsion with the second water-in-oil emulsion. If desired, one or more additional water-in-oil emulsions can be mixed with the first and second water-in-oil emulsions. For example, third, fourth, fifth or even more water-in-oil emulsions can be mixed with the first and second water-in-oil emulsions to achieve the final composition.

Advantageously, the pigmented cosmetic composition of the invention is relatively stable such that it desirably does not separate, even over extended periods of time. The composition desirably is able to remain stable even upon exposure to temperature fluctuations (e.g., temperatures above about 50° C. or below about −5° C.). In addition, the composition can be readily applied uniformly and exhibits desirable coverage, skin feel, wear, and appearance characteristics. Also, the present invention permits more than one water-in-oil emulsion to be blended to form a final product. The invention allows for versatility during manufacture such that various quantities of the cosmetic composition can be prepared readily, as desired.

This invention may be best understood with reference to the following detailed description of the preferred embodiments.

DETAILED DESCRIPTION OF THE PREFERRED EMBODIMENTS

The present invention provides a pigmented cosmetic composition comprising a water-in-oil emulsion, and methods related thereto. The pigmented cosmetic composition can be in the form of any of a wide variety of cosmetic products that comprises a water-in-oil emulsion and which contains pigment. By way of example, the beneficial effects of the invention are useful for water-in-oil emulsion products that are in the form of make-ups, such as, but not limited to, foundation, mascara, eye-liner, rouge, concealer, eye-shadow, lipstick, lipcolor and the like, as well as pigmented sunscreen products.

The composition desirably is in the form of a liquid or semi-liquid (e.g., gel), as opposed to a solid or stick formulation. The liquid or semi-liquid composition of the invention can readily be applied uniformly, and exhibits desirable skin feel, wear and appearance characteristics.

The pigmented cosmetic composition in accordance with the present invention comprises a water-in-oil emulsion. As such, the oil phase is the continuous (or external) phase. Dispersed within the oil phase are an aqueous (or internal) phase, pigment particulate, emulsifier, a separation inhibitor comprising a silicone elastomer, and other optional ingredients well known to those skilled in the art that can be included, as desired. It is to be noted that, although the singular is utilized for convenience to describe certain ingredients, it will be appreciated that the use of the singular herein is meant to encompass one or more of the recited ingredient, unless otherwise indicated.

In accordance with the present invention, the silicone elastomer provides the surprising and unexpected result of enhancing the stability of the water-in-oil product, despite the presence of the relatively heavy pigment in the composition. Particularly, the pigmented cosmetic composition of the invention remains stable in such a way that separation of the oil phase, aqueous phase, and pigment is minimized or eliminated, even over extended periods of time. Preferably, the composition remains stable for at least three months, more preferably, for at least six months, still more preferably, for at least nine months, and even more preferably, for at least twelve months. Furthermore, the cosmetic composition of the present invention remains stable and, thus, does not separate even when subjected to temperature fluctuations, such as, for example, temperatures above about 40° C., more preferably, temperatures above about 50° C., or temperatures below about 0° C., more preferably, temperatures below about −5° C.

The oil phase can be in any suitable form. For example, the oil can be selected from silicone oils, mineral oils, branched paraffins, hydrocarbons, petroleum oils, vegetable oils, ethers, esters, and the like, and mixtures thereof. Suitable oils, as will be appreciated by one of ordinary skill in the art, are described, for example, in U.S. Pat. Nos. 5,980,921 and 6,042,815. Preferred oils are silicone oils. Silicone oils can be in the form of one or more volatile silicones, non-volatile silicones, and mixtures thereof. Exemplary silicones include, but are not limited to, cyclomethicone, phenyl trimethicone, dimethicone, alkyl dimethicone, fluorinated silicones, and the like, or combinations thereof.

The oil is included in an amount sufficient to serve as the continuous phase in which the aqueous phase, pigment, and any optional ingredients that are included, are dispersed. Preferably, the oil phase is present in an amount of from about 20% to about 95% by weight of the composition, and, more preferably, in an amount of from about 30% to about 40% by weight of the composition.

The aqueous phase is in the form of aqueous droplets that are dispersed within the continuous oil phase. In addition to water, the droplets of the aqueous phase also optionally can include other ingredients, such as, for example, alcohols, glycols, or combinations thereof. Such additives can provide, for example, desirable stabilizing, humectant, and preservative solubilizing advantages. For example, suitable alcohols that may be included in the aqueous phase include, but are not limited to, ethanol, isopropanol, and the like, or combinations thereof. Suitable glycols that may be included in the aqueous phase include, but are not limited to, propylene glycol, butylene glycol, pentylene glycol, hexylene glycol, or the like (including, for example, isomers thereof), or combinations thereof. The alcohol and/or glycol preferably make up less than about 20% by weight of the aqueous phase, and, more preferably, less than about 10% by weight of the aqueous phase. Further, the amount of the aqueous phase in the composition preferably is from about 5% to about 70% by weight of the composition, more preferably, from about 30% to about 50% by weight of the composition.

The composition also includes an emulsifier to maintain the aqueous droplets in a relatively uniform distribution within the oil phase. As will be appreciated by one of ordinary skill in the art, the emulsifier is selected to be compatible with the type of oil utilized in the oil phase. Any of a number of emulsifiers can be utilized, depending upon the type of oil in the oil phase. Emulsifiers can be nonionic, anionic, or cationic. Suitable emulsifiers are disclosed, for example, in U.S. Pat. Nos. 3,755,560 and 4,421,769, as well as McCutcheon's Detergents and Emulsifiers, North American Edition, pages 317-324 (1986). Strictly by way of example, cetyl-dimethicone copolyol (e.g., ABIL WE-09, commercially available from Goldschmidt) is an exemplary emulsifier that can be selected, particularly in conjunction with the use of a silicone oil. The emulsifier is provided in an amount that is sufficient to emulsify the aqueous droplets in the continuous oil phase. For example, the emulsifier can be present in an amount of from about 2% to about 20% by weight of the composition, more preferably, in an amount of from about 3% to about 6% by weight of the composition.

The pigment particulate is included for the purpose of applying color in the case of make-up, or, in the case of a sunscreen product, it is in "invisible" form to attenuate potentially harmful ultraviolet rays. Any suitable organic or inorganic pigment can be included in the water-in-oil emulsion of the invention. By way of example, and not by way of limitation, the pigment can be selected from titanium dioxide, yellow iron oxide, red iron oxide, black iron oxide, zinc oxide, talc, mica, magnesium carbonate, calcium carbonate, magnesium silicate, aluminum magnesium silicate, silica, ultramarine, nylon powder, polyethylene powder, polystyrene powder, silk powder, crystalline cellulose, starch, titanated mica, iron oxide titanated mica, bismuth oxychloride, or the like, and combinations thereof. As will be appreciated by one of ordinary skill in the art, in embodiments where the pigment serves as a particulate sunscreening agent, the pigment can be selected from, for example, metal oxides such as zinc oxide, titanium dioxide, or the like, or combinations thereof.

Preferably, the pigment is treated to promote its dispersion in the oil phase and to avoid its entry into the aqueous phase of the emulsion. The presence of the pigment in the aqueous phase is undesirable because the resulting product may tend to form streaks. The particular type of surface treatment will vary depending upon the type of oil employed in the oil phase, as will be appreciated by one of ordinary skill in the art. Hydrophobic treatment is preferred to facilitate dispersion of the pigment in the oil phase. Useful hydrophobic pigment treatments are described, for example, in U.S. Pat. No. 5,143,722. For example, in the case of a silicone oil phase, the pigment can be treated with a silicone such as methicone, or the like.

Pigment particulate can be provided in any suitable amount in the composition. For example, the pigment can be present in an amount of from about 1% to about 50% by weight of the composition, more preferably, in an amount of from about 5% to about 15% by weight of the composition.

In accordance with the present invention, the pigmented composition includes a separation inhibitor comprising a silicone elastomer. As will be appreciated by one of ordinary skill in the art, "elastomers" generally are defined as chain polymers having a degree of cross-linking sufficient to provide a rubber-like material. The silicone elastomer provides a secondary structure which stabilizes the pigment so that it remains dispersed in the oil phase and does not cause separation of the emulsion due to the heavy weight of the pigment relative to the weight of the other components of the emulsion. While not wishing to be bound by any particular theory, it is believed that the flexible nature of the silicone elastomer, which resembles a jelly-like consistency, permits the pigment to remain dispersed in the oil phase while not making the emulsion so thick that its ability to be uniformly applied is compromised.

Any suitable silicone elastomer can be utilized in the practice of the invention. Suitable silicone elastomers generally are disclosed in, for example, U.S. Pat. Nos. 4,742,142; 4,980,167; 5,266,321; 5,599,533; and 6,042,815. The elastomers generally are at least partially cross-linked and preferably are the reaction product of an organopolysiloxane having unsaturated groups such as vinyl or allyl, preferably bonded to another Si atom, and another silicon compound capable of participating in the addition reaction, for example, an organohydrogenpolysiloxane. By way of example, the silicone elastomer can be in the form of a dimethicone cross-polymer, dimethicone/vinyl dimethicone cross-polymer, dimethicone/phenyl vinyl dimethicone cross-polymer, dimethicone copolyol cross-polymer, alkyl dimethicone copolyol cross-polymer (e.g., lauryl dimethicone copolyol cross-polymer), alkyl dimethicone/vinyl dimethicone cross-polymer (e.g., cetearyl dimethicone/vinyl dimethicone cross-polymer), divinyldimethicone/dimethicone cross-polymer, polysilicone 11, or the like, or combinations thereof. Dimethicone cross-polymers are preferred.

The separation inhibitor preferably also comprises a carrier for the silicone elastomer. Desirably, the carrier can be in the form of a solvent that is compatible with the selected silicone elastomer. For example, where the silicone elastomer is in the form of a dimethicone cross-polymer, a suitable carrier can be selected from a solvent such as, but not limited to, cyclomethicone. The carrier preferably is selected to enhance the jelly-like consistency of the separation inhibitor. A preferred separation inhibitor is DC-9040, commercially available from The Dow Chemical Company, which includes approximately 87% of cyclomethicone solvent and approximately 13% of a dimethicone cross-polymer.

The silicone elastomer of the separation inhibitor is present in an amount that is sufficient to enhance the stability of the pigment so that it remains dispersed in the oil phase. For example, the silicone elastomer can be included in an amount of from about 0.1% to about 7% by weight of the composition, more preferably, in an amount of from about 1% to about 2% by weight of the composition.

Although not essential, the pigmented cosmetic composition of the invention also can include one or more optional ingredients, such as, for example, sunscreening agent, thickener, inorganic salt, preservative, fragrance, vitamin, feel and/or appearance enhancer, or the like. If desired, thickener can be included, for example, to adjust the viscosity of the composition. The composition can have any suitable viscosity. Preferably, the viscosity of the composition is from about 500 cps to about 100,000 cps, more preferably, from about 1,000 cps to about 10,000 cps.

If included, any suitable thickener can be utilized in accordance with the present invention. By way of example, the thickener can be in the form of any of a number of suitable waxes (e.g., silicone waxes when used with silicone oils), fatty alcohols, or the like, which are compatible with the oil phase as will be appreciated readily by one of ordinary skill in the art. Especially suitable thickeners include, but are not limited to, cetyl alcohol, bentone gel, and the like, or combinations thereof. The thickener can be provided in any suitable amount to achieve the desired viscosity for the composition. Preferably, the composition excludes thickener or includes thickener in relatively small amounts, such as, for example, less than about 10% by weight of the composition. For example, in some embodiments, the thickener can be included in an amount of from about 1% to about 10% by weight of the composition, more preferably, in an amount of from about 3% to about 8% by weight of the composition.

In embodiments where the pigmented cosmetic composition is in the form of a make-up, a sunscreening agent is optionally included. Suitable sunscreening agents that are approved in a particular country will be readily appreciated by one of ordinary skill in the art. By way of example, but not by way of limitation, the sunscreening agent can be selected from octyl methoxycinnamate, Avobenzone, methyl anthranilate, Octocrylene, octyl salicylate, Oxybenzone, Padimate O, as well as invisible pigments as discussed herein above, such as, for example, micronized metal oxides, including, but not limited to, micronized titanium dioxide, micronized zinc oxide, or the like, or any combination thereof. The sunscreening agent is selected to be compatible with the oil phase. If included, the sunscreening agent can be provided in any suitable amount, such as, for example, in an amount of from about 1% to about 35% by weight of the composition, more preferably, in an amount of from about 5% to about 15% by weight of the composition.

In some embodiments, inorganic salts are included in the aqueous phase to enhance the formation of the water-in-oil emulsion. The inorganic salt can be selected from any of a variety of inorganic salts, such as, for example, sodium chloride, magnesium chloride, magnesium sulfate, or the like, or combinations thereof. The inorganic salt is provided in any suitable amount, such as, for example, in an amount of from about 0% to about 4% by weight of the composition, more preferably in an amount of from about 0.5% to about 2% by weight of the composition.

In addition, the composition optionally can include a preservative. For example, the preservative can be selected to kill bacteria that might otherwise be present in the water-in-oil emulsion. Although water-in-oil emulsions as in the present invention are less susceptible to sustaining bacteria multiplication than oil-in-water emulsions, bacteria nevertheless can exist in water-in-oil emulsions. Accordingly, preservatives can be included, if desired, for example, to kill any bacteria that might otherwise be present.

One of ordinary skill in the art will readily appreciate examples of suitable preservatives. The preservative can be provided in any suitable amount, such as, for example, from about 0% to about 2% by weight of the composition, more preferably, in an amount of from about 0.5% to about 1.5% by weight of the composition.

The composition can also optionally include fragrance, vitamin, and feel and/or appearance enhancer, as desired. One of ordinary skill in the art will readily appreciate suitable examples of these types of additives. The vitamin and the fragrance each can be provided in any suitable amount, such as, for example, from about 0% to about 5% by weight of the composition. The feel and/or appearance enhancer, if included, for example, in the form of particle balls, provides improved aesthetics during application and/or scatters light to provide a soft focus effect that diminishes the appearance of wrinkles, as will be appreciated by one of ordinary skill in the art. The feel and/or appearance enhancer can be included in any suitable amount, such as, for example, from about 0% to about 10% by weight of the composition, more preferably, from about 1% to about 5% by weight of the composition.

The present invention also permits preparation of the water-in-oil cosmetic composition by mixing two or more pigmented water-in-oil emulsions of different colors, if desired. In the inventive method, two or more pigmented water-in-oil emulsions are prepared separately. In some embodiments, three, four, five, or more water-in-oil emulsions of different colors are prepared separately. At least one of the water-in-oil emulsions comprises a separation inhibitor comprising the silicone elastomer, in accordance with the present invention. Preferably, however, each of the emulsions contains the separation inhibitor comprising the silicone elastomer to optimize separation inhibition. Each of the separate water-in-oil emulsions includes an oil phase as the continuous phase, as well as an aqueous phase, emulsifier, and pigment, as described herein. The oil phase, aqueous phase, emulsifier, and silicone elastomer in each of the separate emulsions can be the same or different, but preferably the pigment component is different in each of the water-in-oil emulsions. The separately prepared water-in-oil emulsions then are mixed together to form the final pigmented water-in-oil emulsion product. It will be appreciated that, as an alternative, the composition can be prepared in a single batch, where the pigments are all added to the same batch.

The method of preparing the pigmented cosmetic composition according to the invention promotes manufacturing efficiency. For example, water-in-oil emulsions of a single basic color, particularly, black, yellow, white, and red, can be prepared, for example, in a large batch. Then, the separate water-in-oil emulsions of basic colors can be mixed to form the final product of the desired color created by the blend of the separate water-in-oil emulsions. Thus, the method of the invention facilitates preparation of varying quantities, even smaller quantities (e.g., less than 100 gallons), of the end-product.

The following examples further illustrate the present invention, but should not be construed as in any way limiting its scope.

EXAMPLE 1

This example is an illustrative embodiment of the pigmented cosmetic composition of the present invention. The ingredients discussed with respect to this illustrative embodiment are listed in Table 1.

Four separate pigmented water-in-oil emulsions were prepared. The emulsions were the same except that they each had a different pigment (black iron oxide, red iron oxide, yellow iron oxide, and titanium dioxide). For each emulsion, the components were added into a large compounding tank at room temperature without the aid of heat. The oil phase components, emulsifiers, preservatives, and sunscreens were added to the compounding tank and homogenized with a high shear motor stator mixer or colloid mill mixer. The pigment was added and the batch was mixed until the additives were suspended in the oil. Premixed aqueous phase was slowly added to the batch while being homogenized with the high shear motor stator mixer (or colloid mill mixer). Water soluble preservatives were added followed by the separation inhibitor (DC 9040). The remaining ingredients then were added. The four emulsions then were mixed under high shear to form the final composition. The formulation is set forth in Table 1.

TABLE I

Exemplary Formulation

| Ingredient | Type | CTFA NAME | WT. % |
|---|---|---|---|
| Witch Hazel | Aqueous phase | Witch Hazel Distillate (14% alcohol) | 45.9870 |
| DC 9040 Silicone OTC (Dow Corning) | Separation inhibitor comprising silicone elastomer | Cyclomethicone (87% by wt.) (and) Dimethicone Crosspolymer (13% by wt.) | 10.0000 |
| Dow Corning 345 Fluid | Oil Phase | Cyclomethicone | 7.0000 |
| Titanium Dioxide SI2 (Cardre) | Surface-treated pigment | Titanium Dioxide (And) Methicone | 7.0000 |
| Cyclomethicone | Oil Phase | Cyclomethicone | 5.0000 |
| Parsol MCX (Roche) | Sunscreen | Octyl Methoxycinnamate | 5.0000 |
| Abil WE-09 (Goldschmidt) | Emulsifier | Cetyl Dimethicone Copolyol | 4.0000 |
| Bentone Gel VS-5 PC (Elementis Specialties) | Thickener | Cyclomethicone (And) Quarternium-19 Hectorite (And) Propylene Carbonate | 2.5000 |
| Butylene Glycol | Glycol (Aqueous Phase) | Butylene Glycol | 2.5000 |
| Silicone 556 (Dow Corning) | Oil Phase | Phenyl Trimethicone | 2.0000 |
| Gel Base S/L (Brooks) | Oil Phase | Cyclopentasiloxane (And) Dimethylpolysiloxane | 2.0000 |
| Octyl Salicylate (OTC) | Sunscreen | Octyl Salicylate | 2.0000 |
| Orgasol 2002 EXD NAT (DD Chem) | Feel and Appearance Enhancer | Nylon-12 | 1.6000 |
| Sodium Chloride (Cooperative | Inorganic salt | Sodium Chloride | 1.0000 |

TABLE I-continued

Exemplary Formulation

| Ingredient | Type | CTFA NAME | WT. % |
|---|---|---|---|
| Purchasers) | | | |
| Yellow Iron Oxide SI2 (Cardre) | Pigment | Iron Oxide (And) Methicone | 1.0000 |
| Phenoxyethanol | Preservative | Phenoxyethanol | 0.6000 |
| Black Iron Oxide SI2 (Cardre) | Pigment | Iron Oxide (And) Methicone | 0.2000 |
| Methylparaben | Preservative | Methylparaben | 0.2000 |
| Red Iron Oxide SI2 (Cardre) | Pigment | Iron Oxide (And) Methicone | 0.2000 |
| Fragrance | Fragrance | Fragrance | 0.1000 |
| Propylparaben | Preservative | Propylparaben | 0.0500 |
| Disodium EDTA | Preservative | Disodium EDTA | 0.0500 |
| Vitamin A Palmitate (BASF) | Vitamin | Retinyl Palmitate (Corn Oil) | 0.0010 |
| Vitamin E Oil Acetate (Roche) | Vitamin | Tocopheryl Acetate | 0.0010 |
| BV-OSC (Barnet) | Vitamin | Tetrahexyldecyl Ascorbate | 0.0010 |
| Aloe Leaf (Tri-K) | Vitamin | Aloe Barbadensis | 0.0100 |

EXAMPLE 2

This Example demonstrates the inhibition of separation of the present invention.

In particular, six samples of the formulation set forth in Example 1 were prepared as described in Example 1. Each of the six samples was placed in a transparent glass vial. Each sample was stored at different temperature conditions for 92 days. The first sample was stored at 5° C., the second sample at room temperature, the third sample at 40° C., the fourth sample at 45° C., the fifth sample at 50° C., and the sixth sample was subjected to three freeze-thaw cycles. After 92 days, none of the samples exhibited any visible sign of separation.

Thus, as seen in Example 2, pigmented cosmetic compositions according to the invention avoid the onset of separation for an extended period of time, even after exposure to different temperature conditions.

All of the references cited herein, including patents, patent applications, and publications, are hereby incorporated in their entireties by reference.

The use of the terms "a" and "an" and "the" and similar referents in the context of describing the invention are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise described. No language in the specification should be construed as indicating that any non-essential element is essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context.

What is claimed is:

1. A pigmented cosmetic composition comprising a water-in-oil emulsion, said emulsion comprising:
   (a) from about 30% to about 40% by weight of an oil phase;
   (b) from about 30% to about 50% by weight of an aqueous phase;
   (c) from about 5% to about 15% by weight of a pigment;
   (d) from about 3% to about 6% by weight of a cetyl dimethicone copolyol emulsifier; and
   (e) a separation inhibitor comprising a silicone elastomer, wherein the silicone elastomer comprises a dimethicone cross-polymer, and wherein said silicone elastomer is present in an amount of from about 0.1% to about 7% by weight of said composition, wherein the composition is stable for at least three months at about 50° C.

2. The composition of claim 1, wherein the aqueous phase comprises an alcohol.

3. The composition of claim 1, wherein the aqueous phase comprises a glycol.

4. The composition of claim 1, wherein the oil phase comprises a silicone oil.

5. The composition of claim 1, wherein the separation inhibitor further comprises a carrier for the dimethicone cross-polymer.

6. The composition of claim 5, wherein the carrier is cyclomethicone.

7. The composition of claim 1, wherein the pigment is selected from the group consisting of titanium dioxide, yellow iron oxide, red iron oxide, black iron oxide, zinc oxide, talc, mica, magnesium carbonate, calcium carbonate, magnesium silicate, aluminum magnesium silicate, silica, ultramarine, nylon powder, polyethylene powder, polystyrene powder, silk powder, crystalline cellulose, starch, titanated mica, iron oxide titanated mica, bismuth oxychloride, and combinations thereof.

8. The composition of claim 7, wherein the pigment is surface treated.

9. The composition of claim 8, wherein the pigment is surface treated with silicone.

10. The composition of claim 1, wherein the emulsion further comprises a sunscreening agent.

11. The composition of claim 10, wherein the sunscreening agent is present in an amount of from about 5% to about 15% by weight of said composition.

12. The composition of claim 1, wherein the emulsion further comprises a thickener.

13. The composition of claim 12, wherein the thickener is present in an amount of from about 0% to about 10% by weight of said composition.

14. The composition of claim 1, wherein the emulsion further comprises an inorganic salt for enhancing the formation of the water-in-oil emulsion.

15. The composition of claim 14, wherein the inorganic salt is present in an amount of from about 0% to about 4% by weight of said composition.

16. The composition of claim 14, wherein the inorganic salt is selected from the group consisting of sodium chloride, magnesium chloride, magnesium sulfate, and combinations thereof.

17. The composition of claim 1, wherein the emulsion further comprises a preservative.

18. The composition of claim 17, wherein the preservative is present in an amount of from about 0% to about 2% by weight of said composition.

19. The composition of claim 1, wherein the composition is a make-up.

20. The composition of claim 19, wherein the make-up is selected from the group consisting of a foundation, a rouge, a concealer, eye-shadow, eye-liner, a mascara, a lipstick, and a lipcolor.

21. The composition of claim 1, wherein the composition is a sunscreen.

22. A pigmented cosmetic composition comprising a water-in-oil emulsion, said emulsion comprising:
 (a) from about 30% to about 40% by weight of an oil phase;
 (b) from about 30% to about 50% by weight of an aqueous phase;
 (c) from about 5% to about 15% by weight of a pigment;
 (d) from about 3% to about 6% by weight of a cetyl dimethicone copolyol emulsifier; and
 (e) a separation inhibitor comprising a silicone elastomer, wherein the silicone elastomer comprises a dimethicone cross-polymer, and wherein said silicone elastomer is present in an amount of from about 0.1% to about 7% by weight of said composition; and optionally, one or more of the following ingredients:
 (i) a sunscreening agent;
 (ii) a thickener;
 (iii) an inorganic salt;
 (iv) a preservative;
 (v) a fragrance; and
 (vi) a vitamin,
wherein the composition is stable for at least three months at about 50° C.

23. A particulate sunscreen composition comprising a water-in-oil emulsion, said emulsion comprising:
 (a) from about 30% to about 40% by weight of an oil phase;
 (b) from about 30% to about 50% by weight of an aqueous phase;
 (c) from about 1% to about 35% by weight of a particulate sunscreening agent;
 (d) from about 3% to about 6% by weight of a cetyl dimethicone copolyol emulsifier; and
 (e) a separation inhibitor comprising a silicone elastomer, wherein the silicone elastomer comprises a dimethicone cross-polymer, and wherein said silicone elastomer is present in an amount of from about 0.1% to about 7% by weight of said composition, wherein the composition is stable for at least three months at about 50° C.

24. The composition of claim 23, wherein the particulate sunscreening agent is a metal oxide or combinations thereof.

25. The composition of claim 24, wherein the particulate sunscreening agent is selected from the group consisting of zinc oxide, titanium dioxide, and combinations thereof.

26. The composition of claim 23, wherein said emulsion further comprises at least one of the following optional ingredients:
 (i) a pigment;
 (ii) a thickener;
 (iii) a preservative;
 (iv) an inorganic salt;
 (v) a fragrance; and
 (vi) a vitamin.

27. The composition of claim 4, wherein the oil phase comprises cyclomethicone, phenyl trimethicone, cyclopentasiloxane, and dimethylpolysiloxane.

28. The composition of claim 9, wherein the silicone is dimethicone.

29. The composition of claim 10, wherein the sunscreening agent is at least one compound selected from the group consisting of octyl methoxycinnamate and octyl salicylate.

30. The composition of claim 12, wherein the thickener is at least one compound selected from the group consisting of quarternium-19 hectorite and propylene carbonate.

31. The composition of claim 17, wherein the preservative is at least one compound selected from the group consisting of phenoxyethanol, methylparaben, propylparaben, and disodium ethylenediaminetetraacetate (EDTA).

32. A pigmented cosmetic composition comprising a water-in-oil emulsion, said emulsion comprising:
 (a) from about 30% to about 40% by weight of an oil phase comprising cyclomethicone, phenyl trimethicone, cyclopentasiloxane, and dimethylpolysiloxane;
 (b) from about 30% to about 50% by weight of an aqueous phase;
 (c) from about 5% to about 15% by weight of a pigment that is surface treated with a silicone;
 (d) from about 3% to about 6% by weight of a cetyl dimethicone copolyol emulsifier; and
 (e) a separation inhibitor comprising a silicone elastomer, wherein the silicone elastomer comprises a dimethicone cross-polymer, and wherein said silicone elastomer is present in an amount of from about 0.1% to about 7% by weight of said composition wherein the composition is stable for at least three months at about 50° C.

\* \* \* \* \*